(12) United States Patent
Carls et al.

(10) Patent No.: US 7,611,537 B2
(45) Date of Patent: Nov. 3, 2009

(54) SYSTEM, DEVICE, AND METHOD FOR PERCUTANEOUS INTERBODY DEVICE AND NUCLEUS REMOVAL SYSTEM

(75) Inventors: Thomas Carls, Memphis, TN (US); Fred J. Molz, IV, Collierville, TN (US); Matthew M. Morrison, Cordova, TN (US); Jonathan Dewey, Memphis, TN (US); Kent M. Anderson, Memphis, TN (US); Eric C. Lange, Collierville, TN (US); Aurelien Bruneau, Memphis, TN (US)

(73) Assignee: Warsaw Orthopedic, Inc.

( * ) Notice: Subject to any disclaimer, the term of this patent is extended or adjusted under 35 U.S.C. 154(b) by 77 days.

(21) Appl. No.: 11/194,191

(22) Filed: Aug. 1, 2005

(65) Prior Publication Data

US 2007/0027545 A1 Feb. 1, 2007

(51) Int. Cl.
*A61F 2/44* (2006.01)
(52) U.S. Cl. .................................. 623/17.12; 623/17.11
(58) Field of Classification Search .... 623/17.11–17.16
See application file for complete search history.

(56) References Cited

U.S. PATENT DOCUMENTS

| | | | |
|---|---|---|---|
| 6,451,019 B1 * | 9/2002 | Zucherman et al. | 606/249 |
| 6,607,530 B1 * | 8/2003 | Carl et al. | 606/914 |
| 7,238,206 B2 * | 7/2007 | Lange et al. | 623/17.11 |
| 2002/0016583 A1 | 2/2002 | Cragg | |
| 2003/0204189 A1 | 10/2003 | Cragg | |
| 2003/0220649 A1 | 11/2003 | Bao et al. | |
| 2005/0038514 A1 * | 2/2005 | Helm et al. | 623/17.12 |
| 2005/0113928 A1 * | 5/2005 | Cragg et al. | 623/17.16 |
| 2005/0261684 A1 * | 11/2005 | Shaolian et al. | 606/61 |
| 2005/0261768 A1 * | 11/2005 | Trieu | 623/17.11 |
| 2006/0235388 A1 * | 10/2006 | Justis et al. | 606/61 |

FOREIGN PATENT DOCUMENTS

| | | |
|---|---|---|
| WO | WO 98/20939 | 5/1998 |
| WO | WO 00/67651 | 11/2000 |
| WO | WO 03/088878 A1 | 10/2003 |
| WO | WO 2004/028414 A1 | 4/2004 |
| WO | WO 2004/043271 | 5/2004 |
| WO | WO 2004/058045 | 7/2004 |

* cited by examiner

*Primary Examiner*—Eduardo C Robert
*Assistant Examiner*—Jerry Cumberledge

(57) ABSTRACT

One embodiment of the present application includes: performing a medical procedure on a segment of a patient's spine. This segment includes two vertebrae each in contact with a spinal disk positioned in an intervertebral disk space. A passage is formed that follows a pathway through the vertebrae and the intervertebral disk space. This passage extends from an extradiscal opening through one of the vertebrae along a path that turns to change direction. The tubular device is inserted in the passage and extends through the intervertebral disk space. A fluid material is introduced into the tubular device to at least partially fill it to provide a spinal prosthetic structure. Other embodiments and inventive aspects include other prosthetic device arrangements, implantation methods, systems, and techniques.

21 Claims, 5 Drawing Sheets

SYSTEM, DEVICE, AND METHOD FOR PERCUTANEOUS INTERBODY DEVICE AND NUCLEUS REMOVAL SYSTEM

BACKGROUND

The present invention relates to a prosthetic device and manner of using the same, and more particularly, but not exclusively, relates to a prosthetic tubular device that is expanded while extending through at least two vertebrae and a spinal disk positioned between these vertebrae.

The use of prosthetic implants to address orthopedic injuries and ailments has become commonplace. Nonetheless, there is an ever-present challenge to enable less invasive surgical techniques, shorten the time required to surgically implant prosthetic devices, decrease patient recovery time, and/or provide other improvements. Thus, there is a need for additional contributions in this area of technology.

SUMMARY

One embodiment of the present application is a unique prosthesis. Other embodiments include unique methods, systems, devices, kits, and apparatus involving an implantable prosthesis.

A further embodiment of the present application includes forming a passage through two vertebrae and a spinal disk positioned in an intervertebral disk space, such that each vertebrae includes an endplate in contact with the spinal disk. The passage extends from an extradiscal opening in one of the vertebrae to the other vertebrae. A tubular device is inserted in the passage to position it through the endplates and the intervertebral disk space. While the tubular device is so positioned, it is at least partially filled with the fluid material that hardens to provide a spinal prosthetic structure. In one form, the passage has an approximate C-shape and also intersects another extradiscal opening in the other of the vertebrae. Alternatively or additionally, in another form of this embodiment the tubular device is structured to expand in at least the intervertebral disk space to form a bulge that serves as a prosthetic discal nucleus.

Another embodiment of the present application includes: performing a medical procedure on a patient's spine that includes two vertebrae each in contact with a spinal disk positioned in an intervertebral space between the vertebrae, forming a passage through the vertebrae and the intervertebral disk space, removing at least a portion of the disk from the intervertebral disk space, inserting a tubular device in the passage that extends through the intervertebral disk space, introducing a fluid material into the tubular device to at least partially fill it, and expanding the tubular device to provide a bulge that serves as a prosthetic structure in place of at least some removed portion of the disk.

Still another embodiment is directed to a kit for performing a spinal implantation procedure that includes one or more instruments to form a passage through two vertebrae and a disk that is positioned between these vertebrae, apparatus to remove at least a portion of a nucleus of the disk, a source of fluid material that cures to form a solid, and an expandable tubular device sized to extend through the passage that includes an end portion defining an opening to receive the fluid material after insertion of the tubular device in the passage and another portion structured to expand and form a bulge when the fluid material cures therein. This bulge is structured to provide a prosthetic substitute for removed discal nucleus tissue.

In yet a further embodiment of the present application, a system of spinal implantation comprises an expandable tubular device sized to extend through a passage. This passage is formed through two vertebrae and a spinal disk in contact with each of these vertebrae and positioned between them. The tubular device contains material that is placed in the tubular device while in a fluid form and cures to form a solid structure as defined by the tubular device extending through the passage. In one form the system further includes one or more interspinous prosthetic devices implanted in the patient's spine and/or structuring of the tubular device to form a bulge that is effective to serve as a prosthetic substitute for removed disk tissue.

One object of the present application is to provide a unique prosthesis.

Alternatively or additionally, another object of the present application is to provide a unique prosthetic method, system, device, instrument, kit, and/or apparatus.

Further embodiments, forms, features, aspects, benefits, objects, and advantages of the present application shall become apparent from the detailed description and figures provided herewith.

DETAILED DESCRIPTION OF SELECTED EMBODIMENTS

Figure 1:
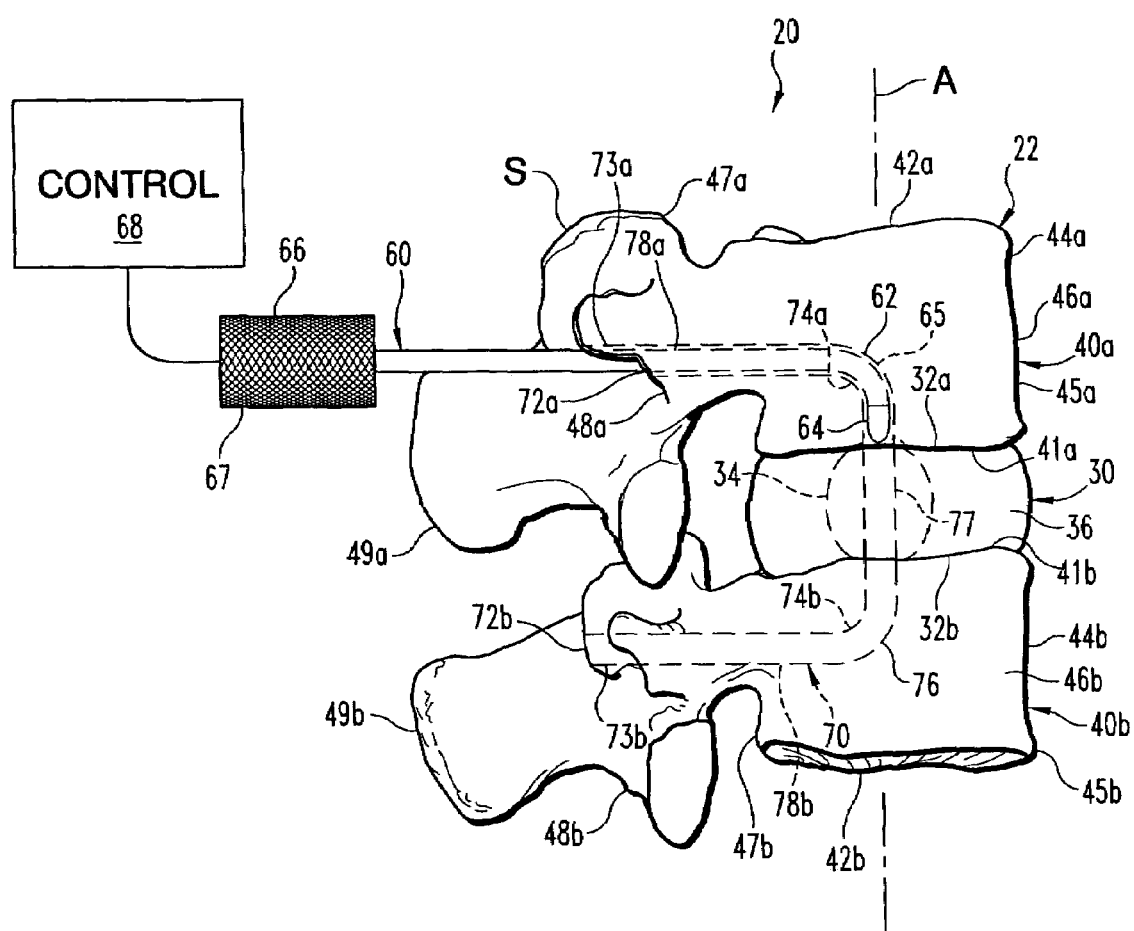
FIG. 1 is a partial, diagrammatic view of a spinal segment with a passage formed through the segment in accordance with a spinal implantation procedure.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 illustrates a portion of spinal implantation system 20 at one stage of a spinal implantation procedure. System 20 is partially shown in FIG. 1 relative to spinal segment 22 of a patient's spine S. Segment 22 extends along axis A, which corresponds to the medial plane of the patient. When spine S is properly functioning, its natural motions include flexion, extension, left and right lateral bending, and axial rotation about axis A. Spinal segment 22 includes spinal disk 30 with superior surface 32a opposing inferior surface 32b. Also, spinal disk 30 internally includes nucleus 34 that is represented in phantom in FIG. 1.

Generally, spinal disk 30 occupies intervertebral disk space 36 defined between vertebrae 40a and 40b. Correspondingly, vertebrae 40a and 40b have inferior endplate 41a and superior endplate 41b, respectively. Inferior endplate 41a of vertebra 40a is in contact with superior surface 32a of spinal disk 30, and superior endplate 41b of vertebra 40b is contact with inferior surface 32b of spinal disk 30.

Vertebrae 40a and 40b each have a corresponding vertebral body 42a and 42b, respectively. Vertebrae 40a and 40b include respective sidewalls 44a and 44b. Further, vertebrae 40a and 40b each include a corresponding anterior portion 45a or 45b. Anterior portions 45a and 45b define anterior boundaries 46a and 46b; respectively. Opposite anterior portions 45a and 45b are corresponding posterior portions 47a and 47b of the respective vertebrae 40a and 40b. Posterior portions 47a and 47b define respective posterior boundaries 48a and 48b. Also, posterior portions 47a and 47b include the typical anatomy of spinal vertebrae including spinous processes 49a and 49b as designated by reference numeral.

System 20 includes bone removing instrument 60. Instrument 60 includes at least one superelastic and/or shape memory member 62 to form and/or readily navigate a curved passageway through vertebrae. For instrument 60, head 64 is utilized to remove bone through cutting, boring, abrasion, ablation, or such different technique as would occur to those skilled in the art. Head 64 is located at the termination of distal end portion 65 of instrument 60. Head is not shown in phantom to enhance clarity. Opposite distal end portion 65, handle 66 of instrument 60 is located along proximal end portion 67. Further, handle 66 is coupled to control device 68. Control device 68 is utilized to control tissue removal with head 64, to guide head 64 along a desired pathway, and/or to perform other operations as would occur to those skilled in the art.

In one form, instrument 60 is manually operated, not requiring a source of external power; however, in other forms instrument 60 is of the powered variety requiring an external power source. In one particular form, instrument 60 includes one or more electrically powered motors to operate head 64, and head 64 is of a rotating cutter type that pivots to control the direction of cutting and correspondingly the resulting direction/curvature of a passageway formed therewith. As an addition or alternative, member 62 is configured of a shape memory alloy that takes on the form of a curved shape in response to an imposed temperature range. This curved form can be selectively constituted to use to urge head 64 along a curved direction. In still other embodiments, instrument 60 may be directed by one or more "steerable" cables or wires, such as the time used for some endoscopes to name just one example or otherwise; include one or more controlled pivot couplings to form a curved passageway; and/or be powered pneumatically, hydraulically, by a combination of any of the previously described techniques, and/or by a different a technique as would occur to those skilled in the art.

As illustrated in FIG. 1, instrument 60 has been applied to form passage 70 through spinal segment 22, as represented in phantom form. For this illustration, distal end portion 65 (excluding head 64) is also shown in phantom where positioned in passage 70. Head 64 is diagrammatically represented in solid line form to enhance clarity. Passage 70 extends between extradiscal openings 72a and 72b. Openings 72a and 72b are each formed through a respective one of posterior boundaries 48a and 48b. Passage 70 extends from each posterior boundary 48a and 48b in an anterior direction away from each respective extradiscal opening 72a and 72b.

Furthermore, passage 70 changes direction as it advances through vertebral bodies 42a and 42b, as represented by passage turns 74a and 74b, to provide a C-shaped side profile from a particular view plane (i.e. the mirror image of that shown in FIG. 1). Between passage turn 74a and 74b, central portion 77 of passage 70 extends. Central portion 77 has a longitude approximately parallel to axis A.

The arrangement of system 20 as illustrated in FIG. 1 corresponds to a stage of the implantation procedure in which passage 70 has been formed or is undergoing formation using instrument 60. It should be noted that passage 70 extends through disk 30 and corresponding nucleus 34 along central portion 77. Passage 70 further includes end portions 78a and 78b, that each open into a corresponding extradiscal opening 72a and 72b. In one process to make passage 70, (a) head 64 of instrument 60 starts at posterior boundary 48a and advances to form opening 72a, portion 78a, turn 74a, and at least part of portion 77, (b) instrument 60 is then withdrawn through opening 72a, (c) next, head 64 starts at posterior boundary 48b and advances to form opening 72b, portion 78b, turn 74b, and at least part of portion 77 joining the portion previously formed, and (d) instrument 60 is then withdrawn through opening 72b. Many alternative processes can be practiced, including directing head 64 along a C-shaped pathway through segment 22 from one of openings 72a or 72b to the other of openings 72a or 72b without withdrawal. In one form, extradiscal openings 72a and 72b are formed through respective pedicles 73a and 73b of corresponding vertebrae 40a and 40b. After passage 70 has been formed, instrument 60 is typically withdrawn to facilitate performance of a subsequent stage of the implantation procedure.

Figure 2:
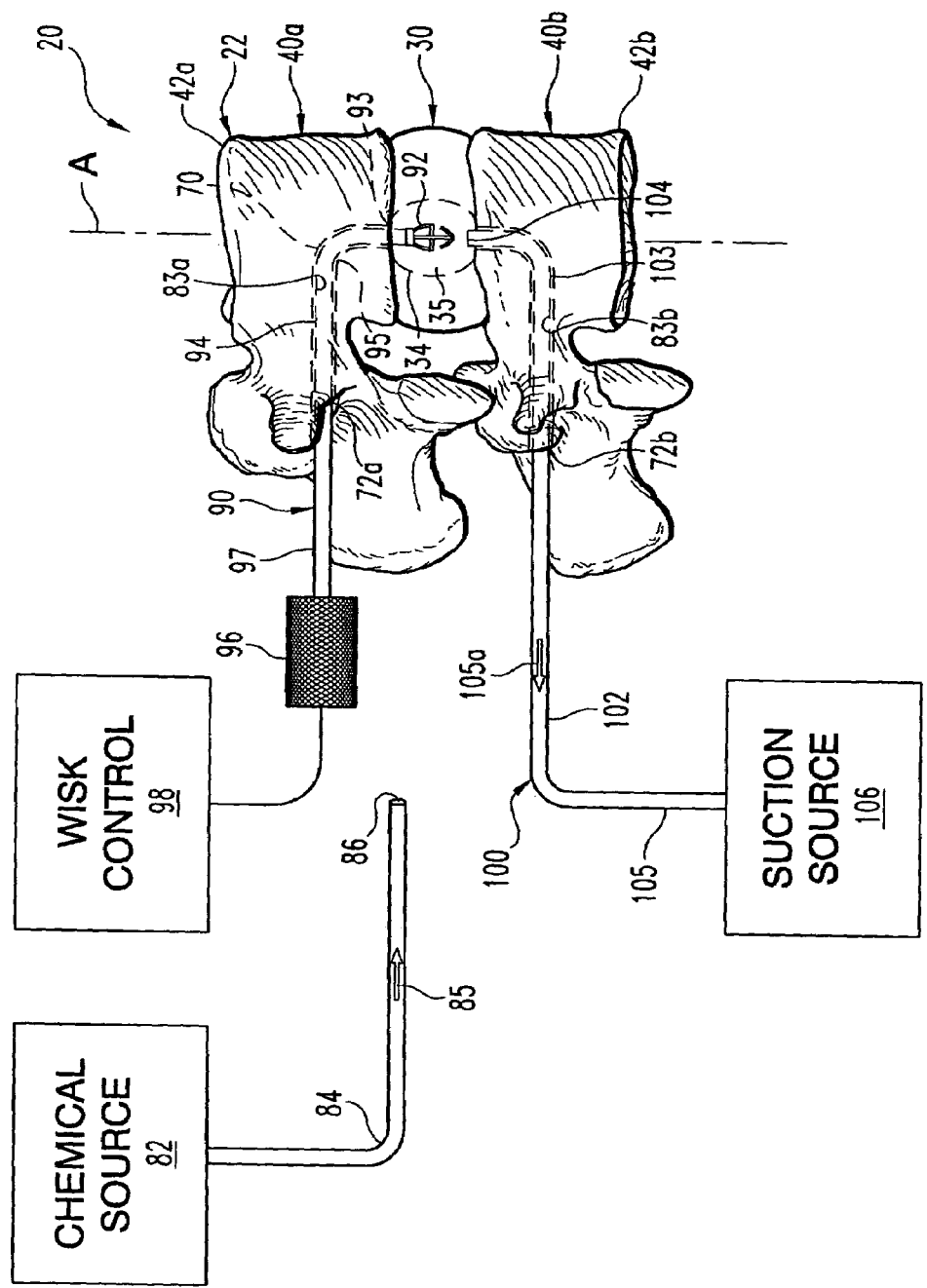
FIG. 2 is a partial, diagrammatic view of the spinal segment of FIG. 1 corresponding to the removal of discal tissue during the procedure.

Referring additionally to FIG. 2, spine segment 22 is shown at a different stage of the implantation procedure; where like reference numerals refer to like features previously described. Also, a different arrangement of system 20 is illustrated to perform this stage of the procedure. For instance, system 20 includes discal tissue removal apparatus 80 in FIG. 2, with portions extending through vertebrae 40a and 40b along passage 70 being shown in phantom. Apparatus 80 is comprised of several components, including chemical source 82 that controllably supplies a fluid chemical material. This chemical material alters tissue of disk 30 to facilitate removal if placed in contact therewith. In one form, the chemical substance provided from source 82 includes one or more digestive enzymes in a liquid or slurry effective to liquefy, dissolve or otherwise breakdown at least a portion of nucleus 34 so that it can be readily removed in a fluid form through passage 70. Source 82 is coupled to conduit 84 to supply the chemical material through conduit outlet 86 in the direction indicated by arrow 85. Conduit 84 and/or outlet 86 are not shown inside passage 70 in the view of FIG. 2 to enhance clarity. Source 82 can provide the chemical material as any type of fluid, including a liquid, slurry, powder, gas, or a combination of these, to name only a few. Source can include a power source to selectively deliver the material by pressurizing it, rely on a gravity to feed it, and/or siphoning—to list some examples.

Apparatus 80 also includes whisk device 90. Whisk device 90 includes a rotatable, vibratory, and/or oscillating whisk head 92 along its distal end portion 93. Whisk head 92 is selectively used to agitate and intermix the chemical material supplied from source 82 with internal discal tissue to enhance removal. One or more superelastic and/or shape memory members 94 can be included along the body of whisk device 90 to aide with advancement of whisk head 92 through passage 70.

Opposite distal end portion 93, whisk device 90 has proximal end portion 97. At proximal end portion 97, operator handle 96 is included. Whisk control 98 is coupled to handle 96 to regulate operation of device 90. Device 90 may be manually, electrically, hydraulically, pneumatically, or otherwise powered. In one particular form, control 98 includes an electromechanical device, such as an electric motor, that is mechanically linked via the body of device 90 to whisk head 92 in a manner to controllably provide the desired movement thereof. The part of whisk device 90 extending through vertebra 40a is shown in phantom in passage 70; however, head 92 is diagrammatically represented in solid line form to enhance clarity. The body of device 90 extending between handle 96 and head 92 can be made steerable or is otherwise guided along curved passage 70 using any of the techniques described in connection with instrument 60, or using other techniques. Device 90 can be combined with source 82. In one nonlimiting example of such a combination, the tissue-altering chemical is provided through a conduit connected to head 92 in an integrated instrument.

Apparatus 80 also includes suction device 100. Suction device 100 includes conduit 102 with distal end portion 103 defining suction inlet 104. Fluid carrying the chemically altered discal tissue and/or mechanically divided discal tissue is evacuated in the direction indicated by arrow 105a. Device 100 includes suction source 106 that is coupled to conduit 102 at its proximal end portion 105. Distal end portion 103 within passage 70 is shown in phantom to enhance clarity. Suction source 106 of device 100 provides the appropriate vacuum level to remove such fluid. Source 106 can also include any further operator controls, power sources, or the like as suitable for the particular application. While not shown, suction device 100 may include one or more operator handles and/or may be combined with one or more of chemical source 82 and device 90. In one particular form of this alternative embodiment, a common conduit is used for the passage of chemicals to the discal tissue and to suction altered tissue and materials out of disk 30. In another form, systematic cutting, ablation, abrasion, or the like may be used to remove discal tissue either with or without chemical alteration. The resulting region from which disk tissue has been removed is designated discal tissue removal region 35.

In one embodiment, apparatus 80 is applied to remove some or all of nucleus 34. One particular form of this application includes the following acts: (a) instrument 60 is used to create extradiscal opening 72a through the corresponding pedicle 73a of the right superior vertebral body 42a and form superior accessway 83a of passage 70 that extends from opening 72a to the superior aspect of nucleus 34 by extending through inferior endplate 41a and superior discal surface 32a; (b) instrument 60 is applied to the left inferior vertebral body 42b to create opening 32b through the corresponding pedicle 73b and form inferior accessway 83b of passage 70 to the inferior aspect of nucleus 34 by extending through superior endplate 41b and inferior discal surface 32b; (c) a digestive enzyme and/or other chemical material(s) to suitably alter nucleus 34 flow through superior accessway 83a of passage 70; (d) after sufficient time for chemical action to take place, suction is applied with suction device 100 through inferior accessway 83b to the inferior aspect of nucleus 34 after it has at least partially been liquefied or altered. Optionally, whisk device 90 can be applied through superior accessway 83a before and/or during suction to enhance removal. Also, if desired to facilitate nucleus 34 removal, additional access may be gained through the left superior and right inferior pedicles of vertebrae 40a and 40b, respectively. After tissue has been removed from disk 30 to the satisfaction of the surgeon, components of apparatus 80 are removed from passageway 70.

Figure 3:
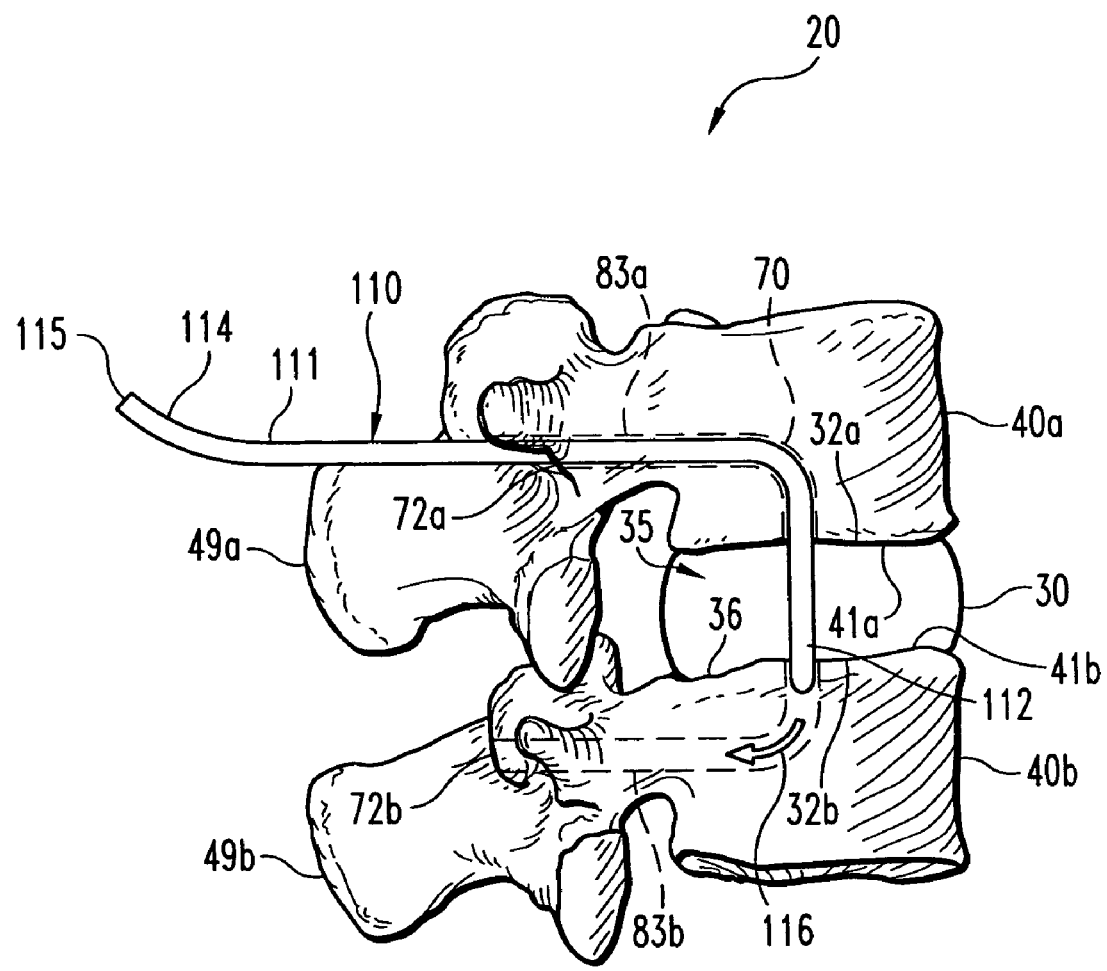
FIG. 3 is a partial, diagrammatic view of the spinal segment of FIG. 1 as a prosthetic tubular device is inserted through the passage during the procedure.

Referring to FIG. 3, other aspects of the spinal implantation procedure are next described; where like reference numerals refer to like features previously discussed. System 20 includes a flexible, expandable tubular device 110. Device 110 is in the form of an elongated balloon 111. After formation of passage 70 and removal of discal tissue at region 35, device 110 is inserted through opening 72a and into superior accessway 83a of passage 70. Within passage 70, device 110 is diagrammatically represented by a solid line to enhance clarity.

Tubular device 110 includes distal end portion 112 opposite proximal end portion 114. Proximal end portion 114 defines opening 115 and distal end portion 112 is closed in this embodiment. Arrow 116 indicates the direction of advancement of tubular device 110 through passageway 70 from extradiscal opening 72a towards extradiscal opening 72b. It should be appreciated that tubular device 110 is of a flexible, resilient type capable of readily being routed through turns 74a and 74b of passage 70. It should be appreciated that the advancement of device 110 through inferior accessway 83b of passage 70 is incomplete in the view of FIG. 3—being representative of device insertion as it is performed. One or more other devices (not shown), can be used to push, pull, guide or otherwise assist the movement of device 110 through passage 70.

Figure 4:
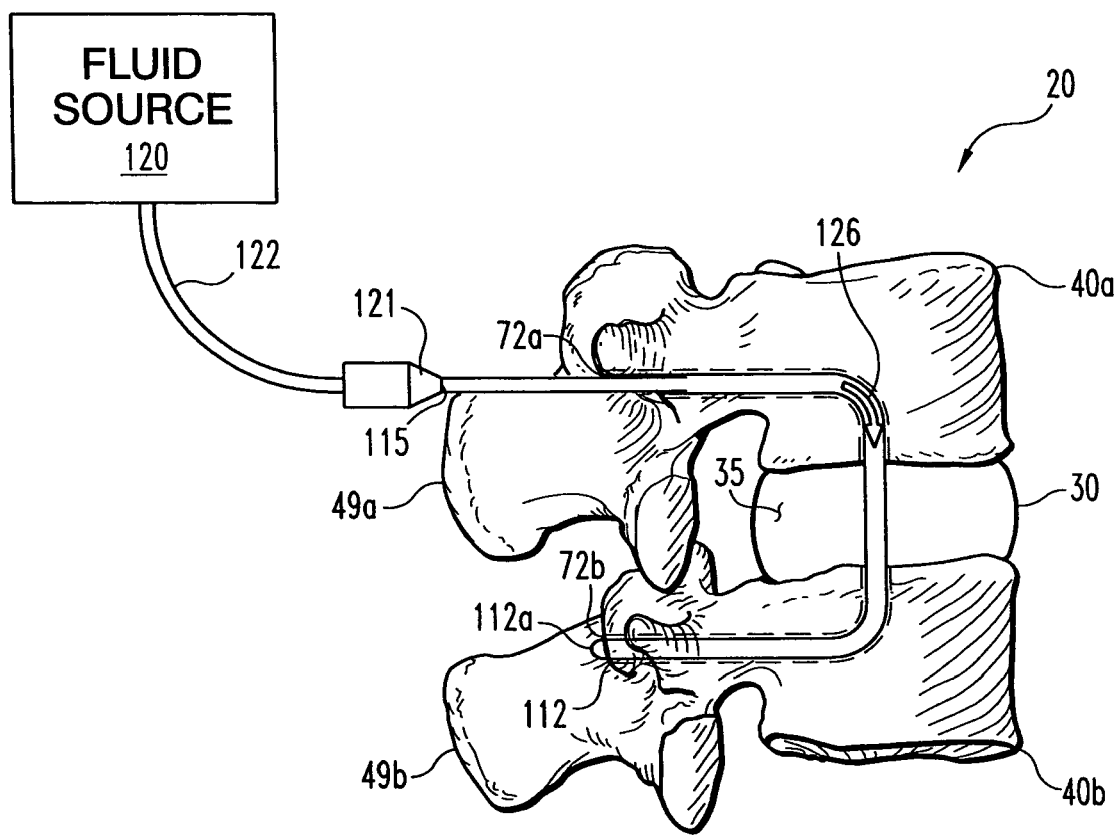
FIG. 4 is a partial, diagrammatic view of the spinal segment of FIG. 1 corresponding to the introduction of a fluid material into the inserted tubular device during the procedure.

Referring to FIG. 4, advancement of device 110 is complete, with closed end 112a of distal end portion 112 having reached opening 72b. System 20 also includes fluid source 120 as shown in FIG. 4. Fluid source 120 is coupled to opening 115 of tubular device 110 by coupling 121 to introduce a fluid material that is used in conjunction with device 110 to provide a prosthetic structure. This fluid material flows from source 120 to device 110 via conduit 122. Because tubular device 110 has closed end 112a, the fluid material accumulates in tubular device 110 as it is deposited, backing-up in a direction opposite the flow path. Fluid may be provided by manual or powered pressurization, a gravity fed approach, or a different way as would occur to those skilled in the art.

Figure 5:
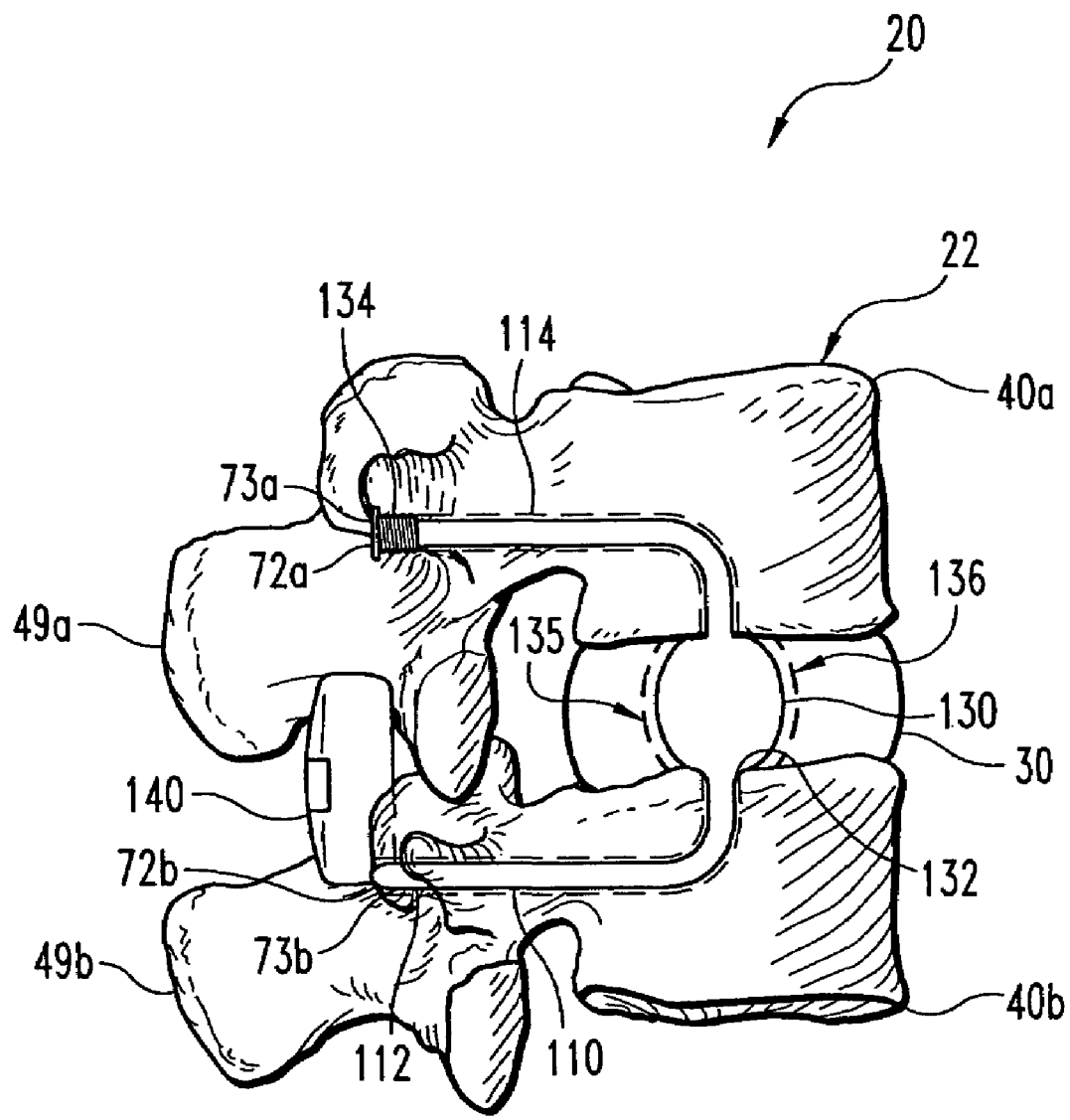
FIG. 5 is a partial, diagrammatic view after the fluid material introduced in FIG. 1 has hardened in the tubular device causing it to expand during the procedure, and further illustrating an anchor device to secure the tubular device to the spinal segment and an interspinous prosthetic device implanted between two spinous processes of the spinal segment.

The fluid material introduced into tubular device 110 is comprised of an epoxy or other polymeric material that hardens as it cures to become a solid after it is deposited. Curing can occur by virtue of an external stimulus, may be largely dependent on the passage of a certain amount of time, and/or other conditions. FIG. 5 shows device 110 after completing deposition of the fluid material therein; where like reference numerals refer to like features, and in which device 110 is again represented in a solid line form to enhance clarity. With the accumulation of fluid material and/or its curing, tubular device 110 is configured to expand so that it conforms to the vertebral structure bordering passage 70. Moreover, tubular device 110 is configured to balloon in region 35 to provide bulge 130 therein. Bulge 130 occurs along central portion 132 of device 110 for the depicted embodiment; however, bulge 130 could be provided at a termination or end portion of tubular device 110. Indeed, in one nonlimiting alternative embodiment, a tubular prosthetic device is advanced through only one of accessways 83 as or 83b with a closed end that expands in response to the filler material to form a bulge in place of nucleus 34. Furthermore, other portions of tubular device 110 can balloon outward into any cavities formed along the margins of passage 70.

As also shown in FIG. 5, the open end of tubular device 110 at end portion 114 has been secured and closed with closure/ anchoring device 134. Device 134 is threaded to engage the corresponding pedicle 73a of vertebrae 40a, which may be prepared using standard techniques. Expansion of device 110 may be enhanced by curing or hardening of the filler material, may only substantially occur with curing or hardening, and/or may be independent of curing or hardening, to name a few possibilities. The expanded form of tubular device 110, being at least partially filled with hardened material is designated prosthetic structure 136 in FIG. 5. FIG. 5 also illustrates interspinous prosthetic device 140 that has been implanted between corresponding spinal processes 49a and 49b. Typically, device 140 is formed from a nonmetallic and resilient organic polymer material; however, other compositions are also contemplated.

In an alternative embodiment, some or all of the fluid material may have different degrees of rigidity and/or resilience as desired for the particular application. In still other embodiments, some or all of the fluid material deposited may not harden or solidify, but rather remain in a liquid, paste, or putty-like state. In one particular form of such an alternative, some or all of the material deposited in device 110 is in a liquid form with a viscosity that increases as it cures. In one form, tubular device 110 is filled with different types of material in different portions of device 110. For example, bulge portion 130 may be filled with a more resilient material than that deposited in portions 78a and 78b and/or such different types of materials may be different phases.

The procedure corresponding to FIGS. 1-5, and system 20, provides an approach to implant prosthetic structure 136 with various adjustable/optimal properties. In one form, it is performed through a minimally-invasive, percutaneous procedure by posterior approach. There are many other embodiments of the present application. For example, passageway 70 may be formed to access region 35 to provide a prosthesis with the formation of passage 70 through only on of vertebrae 40a or 40b. In another example, interspinous prosthetic device 140 may be absent or differently shaped or configured, and/or a different type of construct may be used in conjunction with prosthetic structure 136 such as one or more plates, fixation rod constructs, or like to name just a couple of examples. In yet another example, the implanted tubular device includes two opposing openings in each end that are closed during the procedure. A further example includes multiple devices 136. In one particular instance of multiple prosthetic structures, one extends from the right superior pedicle to the left inferior pedicle through one C-shaped passageway in segment 22, and another extends from the left superior pedicle to the right inferior pedicle. through another C-shaped passageway in segment 22; where such passageways and devices are provided in any of the ways described in connection with FIGS. 1-5. For this particular instance, the prosthetic structures are not only approximately C-shaped in one view plane, but also are collectively oriented to form an approximate X-shape in another view plane. In still other examples, device 110 is configured to deliver or express one or more pharmaceuticals after implantation, only a portion of device 110 is expandable, and/or device 110 is implanted with some fluid already deposited.

In yet a further embodiment, a medical procedure is performed on a spinal segment including two vertebrae each in contact with opposing surfaces of a spinal disk that is positioned in a corresponding intervertebral space. A passage is formed through one of the vertebrae by extending from a posterior boundary towards an interior portion thereof and then turning toward the intervertebral space and passing therethrough into the other vertebrae. The passage again turns to extend towards the posterior boundary of the second vertebrae. For this embodiment, a tubular device is inserted through the passage to extend through the intervertebral disk space and while positioned therein is at least partially filled with fluid material. In one form, this material hardens or changes viscosity to provide a spinal prosthetic structure. In one particular variation, the fluid transforms to provide a solid with a resilient property that is spring-like.

Still another embodiment is directed to apparatus that includes: means for forming a passage through a posterior boundary of one vertebra, through a disk in contact therewith, and through a posterior boundary of another vertebra; means for removing discal tissue through the passage, the discal tissue including at least a portion of a nucleus of the disk; means for providing a prosthetic device in the form of a tubular device that extends through the passage; and means for expanding at least a portion of the tubular device to form a bulge in the disk to provide a prosthetic replacement for at least a portion of the removed discal tissue.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A method, comprising:

performing a medical procedure on a spinal segment including a first vertebra in contact with a spinal disk and a second vertebra in contact with the spinal disk, the spinal disk being positioned in an intervertebral disk space;

forming a passage including a first passage portion extending in an anterior-posterior direction toward an anterior portion of the first vertebra from an extradiscal opening through a posterior boundary of the first vertebra, a second passage portion extending from the first passage portion and passing through the intervertebral disk space and into the second vertebra, and a third passage portion extending from the second passage portion in the anterior-posterior direction toward a posterior boundary of the second vertebra;

inserting a flexible tubular device into the passage and positioning a first end portion of the tubular device in the first passage portion in the anterior-posterior direction, positioning a central portion of the tubular device in the second passage portion and extending through the intervertebral disk space, and positioning a second end portion of the tubular device in the third passage portion in the anterior-posterior direction; and while the tubular device is positioned in the passage, at least partially filling the tubular device with a fluid material and expanding the first and second end portions within the first and third passage portions, respectively, to conform with the vertebral structure bordering said first and third passage portions and expanding the central portion of the tubular device within the second passage portion and ballooning the central portion to provide a bulge in the intervertebral disk space with the first and second end portions extending in the anterior-posterior direction and the central portion extending through the intervertebral disk space to provide a spinal prosthetic structure having a C-shaped configuration.

2. The method of claim 1, wherein the bulge provides a prosthetic structure for at least a portion of a removed nucleus of the disk, and the fluid material hardens to provide a solid in the tubular device as the fluid material cures.

3. The method of claim 1, wherein the third passage portion intersects another extradiscal opening through the posterior boundary of the second vertebra.

4. The method of claim 1, wherein the extradiscal opening is formed through a pedicle of the first vertebra.

5. The method of claim 1, wherein the first end portion of the tubular device includes an opening to receive the fluid material therethrough and further comprising securing the first end portion to the first vertebra adjacent the extradiscal opening.

6. A method, comprising:
performing a medical procedure on a spinal segment including a first vertebra in contact with a spinal disk and a second vertebra in contact with the spinal disk, the spinal disk being positioned in an intervertebral disk space;
forming a passage including a first passage portion extending in an anterior-posterior direction toward an anterior portion of the first vertebra from an extradiscal opening through a posterior boundary of the first vertebra, a second passage portion extending from the first passage portion and passing through the intervertebral disk space and into the second vertebra, and a third passage portion extending from the second passage portion in the anterior-posterior direction toward a posterior boundary of the second vertebra;
inserting a flexible tubular device into the passage and positioning a first end portion of the tubular device in the first passage portion in the anterior-posterior direction, positioning a central portion of the tubular device in the second passage portion and extending through the intervertebral disk space, and positioning a second end portion of the tubular device in the third passage portion in the anterior-posterior direction;
while the tubular device is positioned in the passage, at least partially filling the tubular device with a fluid material to expand the first and second end portions and the central portion of the tubular device within the portions of the passage with the first and second end portions extending in the anterior-posterior direction and the central portion extending through the intervertebral disk space to provide a first spinal prosthetic structure having a C-shaped configuration; and
forming a different passage extending into the first vertebra and the second vertebra and passing through the disk space, and providing a second spinal prosthetic structure through the different passage with an orientation that crosses a path of the first spinal prosthetic structure within the disk space.

7. A method, comprising:
forming a passage through two vertebrae and a spinal disk positioned in an intervertebral disk space, a first one of the vertebrae including a first endplate in contact with the spinal disk and a second one of the vertebrae including a second endplate in contact with the spinal disk, the passage including a first passage portion extending from a first extradiscal aperture in the first one of the vertebrae in an anterior-posterior direction, a second passage portion extending from the first passage portion and passing through the intervertebral disk space, and a third passage portion extending from the second passage portion and into the second one of the vertebrae, wherein the first extradiscal aperture extends through a posterior boundary of the first one of the vertebrae;
inserting a flexible tubular device into the passage and positioning a first end portion of the tubular device in the first passage portion in the anterior-posterior direction, positioning a central portion of the tubular device in the second passage portion and through the first endplate, the intervertebral disk space, and the second endplate, and positioning a second end portion of the tubular device in the third passage portion and into the second one of the vertebrae, wherein the first end portion of the tubular device extends from the first extradiscal aperture toward an anterior portion of the first one of the vertebrae; and
while the tubular device is positioned in the passage, at least partially filling the tubular device with a fluid material and expanding the first and second end portions within the first and third passage portions, respectively, to conform with the vertebral structure bordering said first and third passage portions and expanding the central portion of the tubular device within the second passage portion and ballooning the central portion to provide a bulge in the intervertebral disk space to provide a spinal prosthetic structure with the first end portion extending in the anterior-posterior direction and the central portion extending through the intervertebral disk space.

8. The method of claim 7, which includes removing one portion of the disk before insertion of the tubular device and wherein the tubular device extends through another portion of the disk after the insertion.

9. The method of claim 7, which includes removing at least a portion of the spinal disk from the intervertebral disk space; and
wherein the bulge in the intervertebral disk space between the vertebrae replaces at least a portion of the disk removed from the intervertebral disk space, the bulge having an outer cross section that is larger than the first and third passage portions.

10. The method of claim 7, wherein the first end portion of the tubular device includes an opening to receive the fluid material therethrough and further comprising securing the first end portion to the first one of the vertebrae adjacent the first extradiscal aperture.

11. The method of claim 7, which includes forming a different passage through the vertebrae and intervertebral disk space and providing another prosthetic structure in the different passage that is formed by at least partially filling another tubular device with a fluid.

12. The method of claim 7, wherein the first extradiscal aperture extends through a pedicle of the first one of the vertebrae.

13. The method of claim 7, wherein the passage opens into a second extradiscal aperture extending through a posterior boundary of the second one of the vertebrae.

14. The method of claim 7, wherein the fluid material includes an organic polymer compound that cures to form a solid in the tubular device after said filling.

15. A method, comprising:

forming a passage through two vertebrae and a spinal disk positioned in an intervertebral disk space, a first one of the vertebrae including a first endplate in contact with the spinal disk and a second one of the vertebrae including a second endplate in contact with the spinal disk, the passage including a first passage portion extending from a first extradiscal aperture in the first one of the vertebrae in an anterior-posterior direction, a second passage portion extending from the first passage portion and passing through the intervertebral disk space, and a third passage portion extending from the second passage portion and into the second one of the vertebrae, wherein the third passage portion in the second one of the vertebrae extends in the anterior-posterior direction;

inserting a flexible tubular device into the passage and positioning a first end portion of the tubular device in the first passage portion in the anterior-posterior direction, positioning a central portion of the tubular device in the second passage portion and through the first endplate, the intervertebral disk space, and the second endplate; and while the tubular device is positioned in the passage, at least partially filling the tubular device with a fluid material and expanding the first and second end portions within the first and third passage portions, respectively, to conform with the vertebral structure bordering said first and third passage portions and expanding the central portion of the tubular device within the second passage portion and ballooning the central portion to provide a bulge in the intervertebral disk space to provide a spinal prosthetic structure with the first end portion extending in the anterior-posterior direction and the central portion extending through the intervertebral disk space, and wherein the second end portion of the tubular device is positioned in the third passage portion in the anterior-posterior direction, with the first and second end portions extending in the anterior-posterior direction and the central portion extending through the intervertebral disk space to provide the spinal prosthetic structure with a C-shaped configuration.

16. The method of claim 15, wherein the passage has an approximate C-shape, the fluid material is an epoxy that hardens to form a solid, and the first extradiscal aperture is formed through a pedicle of the first one of the vertebrae.

17. The method of claim 15, which includes removing at least a portion of the disk from the intervertebral disk space; and wherein the bulge in the intervertebral disk space has an outer cross section larger than the first and third passage portions, the bulge providing a prosthetic structure in place of at least some of the removed portion of the disk.

18. The method of claim 7, wherein the removed portion of the disk includes at least part of a disk nucleus and the tubular device extends through a remaining portion of the disk in the intervertebral disk space to replace at least some of the nucleus with the bulge.

19. The method of claim 15, wherein the first end portion of the tubular device includes an end defining an opening to receive the fluid material therethrough and further comprising securing the first end portion to the patient's spine.

20. The method of claim 15, which includes implanting an interspinous prosthetic device and engaging the interspinous prosthetic device between corresponding spinal processes of the two vertebrae.

21. The method of claim 15, wherein the first end portion of the tubular device extends from the first extradiscal aperture toward an anterior portion of the first one of the vertebrae.

* * * * *

UNITED STATES PATENT AND TRADEMARK OFFICE
CERTIFICATE OF CORRECTION

PATENT NO. : 7,611,537 B2
APPLICATION NO. : 11/194191
DATED : November 3, 2009
INVENTOR(S) : Carls et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 79 days.

Signed and Sealed this

Twelfth Day of October, 2010

David J. Kappos
*Director of the United States Patent and Trademark Office*